United States Patent [19]
Boden et al.

[11] Patent Number: 5,656,260
[45] Date of Patent: Aug. 12, 1997

[54] LACTONE INSECT LURES

[75] Inventors: Christopher D. J. Boden, Nottingham; John Chambers, Maidenhead; Paul B. McGreevy; Julie A. Dendy, both of Slough; Ian Stevens, Southampton, all of Great Britain

[73] Assignee: The Minister of Agriculture Fisheries and Food in her Britannic Majesty's Government of the U.K. of Gt. Britain and N. Ireland, England

[21] Appl. No.: 558,941

[22] Filed: Nov. 13, 1995

Related U.S. Application Data

[63] Continuation of Ser. No. 151,997, Nov. 15, 1993, abandoned.

[51] Int. Cl.$^6$ .................................................. A01N 31/08
[52] U.S. Cl. .......................... 424/84; 424/405; 54/183
[58] Field of Search ........................................ 424/84

[56] References Cited

U.S. PATENT DOCUMENTS 4,560,551  12/1985  Pierce et al. ........................... 424/84

OTHER PUBLICATIONS

White et al. 89:267044 Biosis—J. Chem. Ecol 15(3) 1989 999–1014.

*Entomological Society of America*, vol. 18, No. 5, pp. 747–755, 1989 Pierce et al "Production Dynamics of Cucujolide Pheromones and Identification . . . ".

*J. Chemical Ecology*, vol. 14, No. 11, 1988 pp. 2071–2099 Oehschlager et al "Chemical Communication in Cucujid Grain Beetles".

*J. of Economic Entomology*, vol. 83, No. 1, pp. 271–276 Pierce et al "Effect of Aggregation Pheromones on Efficacy of Cardboard Traps for Sawtoothed Grain Beetle".

*J. Of Chemical Ecology*, vol. 15, No. 3, 1989 pp. 999–1013 White et al "Saw Toothed Grain Beetle . . . ".

*J. Of Chemical Ecology*, vol. 17 No. 3, 1991 pp. 581–597 Pierce et al "Fungal Volatiles: Semiochemicals for Stored- -Product Beetles . . . ".

*Primary Examiner*—Neil S. Levy
*Attorney, Agent, or Firm*—Nixon & Vanderhye

[57]  ABSTRACT

Novel multi-component insect lures comprising (3Z,6Z)-dodecadien-12-olide and 13-methyl-(5Z,8Z)-tetradecadien-13-olide together with a fungal volatile selected from the group consisting of 1-octen-3-ol and 3-methylbutanol, wherein the amount of 11-methyl-(3Z,6Z)-dodecadien-11-olide in the composition is substantially zero, and a novel method for production of these pheromones, whereby the cost of active components may be reduced to economically advantageous levels. The lures are particularly effective in attracting saw-toothed grain beetles of group Coleoptera, Cucujidae, particularly species *Oryzaephilus surinamensis*.

24 Claims, 2 Drawing Sheets

II

III

IV

LACTONE INSECT LURES

This is a continuation of application Ser. No. 08/151,997, filed 15 Nov. 1993, now abandoned.

FIELD OF INVENTION

The present invention relates to novel multi-component insect lures comprising pheromones, and to a novel method for production of these pheromones, whereby the cost of active components may be reduced to economically advantageous levels. The lures are particularly effective in attracting saw-toothed grain beetles of group Coleoptera, Cucujidae, particularly species *Oryzaephilus surinamensis*.

BACKGROUND OF THE INVENTION

The saw-toothed grain beetle *Oryzaephilus surinamensis* is a serious pest of stored cereals world-wide, and the major pest of cereals in the UK. In order to combat the threat from the insect it is desirable that infestations be detected at an early stage, with concentrations of insects in grain as low as 0.1 insects per Kg (IPK) needing to be detected. The detection methods currently employed fall short of this target and require the manual inspection of samples taken from bulk grain; typically these detect above 1 IPK. In addition such methods are time consuming and labour intensive, leading to considerable expense in developed economies where labour costs are high.

These shortcomings have led to considerable interest in the production of lures for Oryzaephilus and similar pests whereby the requirement for visual inspection of grain may be eliminated. One of the most promising of these lures comprises the lactones 11-methyl-(3Z,6Z)-dodecadien-11-olide (herein referred to as II), (3Z,6Z)-dodecadien-12-olide (herein referred to as III) and 13-methyl-(5Z,8Z)-tetradecadien-13-olide (herein referred to as IV); being pheromone components of *O. surinamensis*, *O. mercator* and *Cryptolestes turcicus* (see Oehlschlager et al 'Chemical communication in grain beetles' J. Chem. Ecol. 14, 2071 (1988). These form part of a series of structurally related macrolides (see FIG. 1) variously attractive to *O. surinamensis*, and four other cucujids: *O. mercator, C. turcicus, C. pusillus* and *C. ferrugineus*. The attractancy of these lactones to cucujids has led Oehlschlager and Borden to propose the generic term 'cucujolides' for them. Syntheses have been published for each of these lactones and the enantiomers of four, but these do not allow for the gram scale production of either (II) 11-methyl-(3Z,6Z)-dodecadien-11-olide or (III) (3Z,6Z)-dodecadien-12-olide which are particularly targeted at *O.surinamensis*.

The pheromones II and III are relatively unstable even at −20° C., the ring closures required to synthesise them are difficult to perform due to their highly constrained conformations and the highly unusual Z-geometry of their diene system which precludes access by elimination. Furthermore II is homochiral in activity and thus enantiospecificity is required in synthesis for maximal attractancy.

In addition to use of these pheromones, both Pierce et al (Environ. Entomol. 18, 747 (1989); J. Econ. Entomol. 83, 273 (1990)) and White at al (J. Chem. Ecol. 15. 999 (1989)) have studied the effect of the fungal volatile 1-octen-3-ol as attractant for grain beetle. Pierce et al show that 0.1 ng per pitfall olfactometer has no significant attractancy to *O. surinamensis* but 0.1 ng to 10 μg has, while above this weight a significant repellance effect occurs. In UK strains this repellant effect takes place at as low as 100 ng per lure.

Combining a mixture of pheromones II, III and IV with the fungal volatile 1-octen-3-ol in weight ratio 1 to 4, Pierce et al showed that a lure effective across a wide range of dose levels may be provided. Further work showed that volatiles such as 3-methylbutanol (J. Chem. Ecol. 17. 581 (1991)) are also effective in synergising the action of pheromones in this manner. In these and the studies referred to above it is clear that any attractant effect is critically dependant upon the amount of each component, and that increasing or decreasing the amount of any of these can lead to repellancy for one or both sexes of the insect.

OBJECT OF THE INVENTION

It is an object of the invention to provide an insect lure suitable for attracting cucujids, and particularly *O. surinamensis*, that does not require the cucujolide pheromone component II that is difficult to synthesise in commercially acceptable yields.

It is a further object of the invention to provide a method for synthesising all or some cucujolide pheromone components of such an insect lure whereby yields are improved to commercially acceptable level.

SUMMARY OF THE INVENTION

The first of these objects is attained by provision of an insect attractant composition comprising the pheromone lactone compounds (3Z,6Z)-dodecadien-12-olide (herein referred to as III) and 13-methyl-(5Z,8Z)-tetradecadien-13-olide (herein referred to as IV), together with an insect attractant fungal volatile wherein the amount of 11-methyl-(3Z,6Z)-dodecadien-11-olide (herein referred to as II) in the composition is substantially zero. Preferred fungal volatiles are selected from the group consisting of 1-octen-3-ol, 3-octanol and 3-methylbutanol. Preferred volatile is 1-octen-3-ol.

Preferably the weight ratio of III to IV is approximately 1:2 to 1:8, most preferably about 1:4. When the fungal volatile is 1-octen-3-ol it is preferably present in the ratio 1.3 (III+IV): 5 to 10 volatile by weight, preferably 1.3:7.5. Thus a preferred composition is of approximate composition 1:4:29 (III):(IV):1-octen-3-ol by weight.

Using such a composition the inclusion of 11-methyl-(3Z, 6Z)-dodecadien- 11-olide is not required to produce a lure effective in attracting *O.surinamenis*, contrary to previous reports (see Oehlschlager et al), and thus the requirement for the difficult synthesis of this homochiral agent is dispensed with or reduced to more economic levels. Furthermore the preferred compositions of the invention may be used in relatively small quantities thus improving commercial suitability.

Surprisingly, inclusion of fungal volatile in the compositions of ratio of III:IV, as defined above, reverses the previously reported reduction in capture of female beetles when levels of II are reduced or II is deleted from the composition completely. In those studies (J. Chem. Ecol. 15, 1015 (1989)) when higher levels of II (8:1:4) were dispensed with in favour of 1:4 III:IV an overall reduction in beetle capture was recorded. It appears from the present inventors work that use of volatile, eg. 1-octen-3-ol, in suitable ratio reverses this effect and allows omission or reduction in amount of II. Using such a lure in pit-fall olfactometers (as Pierce et al) it is found that a typical optimal amount of components is approximately 1.3 to 130 ng of (III+IV) in 1:4 ratio together with 7.5 ng to 750 ng 1-octen-3-ol per trap; preferably the amount of 1-octen-3-ol is increased in step with the amount of pheromone, whereby maximal capture of beetles is recorded. It will be appreciated that these ratios and the total weight of lure composition may be varied within limits readily found by simple experiment by altering them either side of these optimal values and determining whether attractant effect has been maintained. In full sized traps (see U.S. Pat. No. 5,134,802) 300–500 µg III+IV and 1750–3000 µg fungal volatile are typical optimum quantities.

In addressing the second object of the invention, the present inventors have provided a method for the production of pheromones of the cucujolide group, particularly those of II, III and IV described above, comprising the lactonisation of their corresponding acyclic hydroxy acids wherein the acyclic hydroxy acid is cyclised by reaction in the presence of triphenylphosphine and a di-alkyl azodicarboxylate in an organic solvent wherein the hydroxy acid is added, as a solution, in a controlled manner over a period of time to the azodicarboxylate and triphenylphosphine, also in solvent.

This method provides successful cyclisation giving yields of II, III and IV of 72%, 66% and 71% as opposed to 11%, 18% and 74% for the Yonemitsu method, 8%, 22% and 33–46% for the Corey method and 7–10%, 27% and 33–47% for the Mukaiyama method used previously. References for these methods are Tetrahedron Lett, 28, 4569 (1987); Tetrahedron Lett. 3409 (1976) and Chem. Lett 49 (1976). A similar technique has been reported as being used to form a 14-membered biaryl ether lactone that had otherwise proven impossible to produce (Justus and Steglich (1991) Tetrahedron Lett. Vol 32. 41 pp5781–5784).

Using this technique the present inventors have found that not only can up to a five fold increase in lactone product be obtained, but that product almost free (<2% weight) of diolide impurity is provided. Furthermore, when the method is applied to lactonisation to provide cucujolides in this way, reaction times are reduced to a matter of 6 to 8 hours at ambient reaction temperatures, eg. of only 25° C. In this manner gram quantities of both II and III are readily prepared thus facilitating production of more cost effective lures of the first object of the invention.

It should be noted that the use of such a method as applied to the cyclisation of simpler hydroxy acid molecules does not produce optimal yields; these usually being provided at greater than 90% by acyl activation rather than hydroxy activation as provided here. Thus it is surprising that yields significantly higher than the 59% provided by Justus and Stegler can be achieved in one third of the time they report, yet using simpler acyclic molecules.

The preferred synthesis is applied to pheromones II and III and only requires 5 equivalents of dialkyl azodicarboxylate, whereas Justus and Stegler report use of 7.7 equivalents. The preferred azodi-carboxylate is diethyl diazodicarboxylate (DEAD). Preferably five equivalents of triphenylphosphine are employed in a solvent, preferably toluene, as opposed to Justus and Stegler's 7.5 equivalents. It can be seen that such dramatically improved yield, which is not particularly optimised in the case of II and IV, is far in excess of what would have been expected by those skilled in the art in the light of the inferior yields provided with simple hydroxy acids using DEAD/PPh$_3$ as opposed to acid activation.

EXAMPLES OF THE INVENTION

EXAMPLE 1

Preparation of II: 11-methyl-(3Z,6Z)-dodecadien-11-olide

Figure 1:
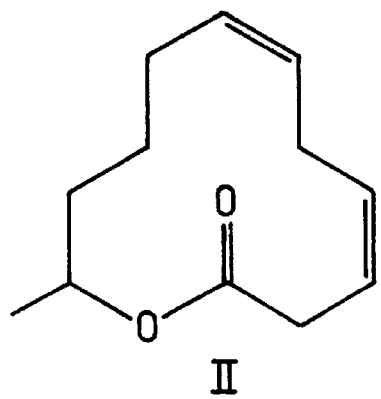
FIG. 1 shows carbon oxygen skeletons of pheromones II, III and IV.
Figure 1:
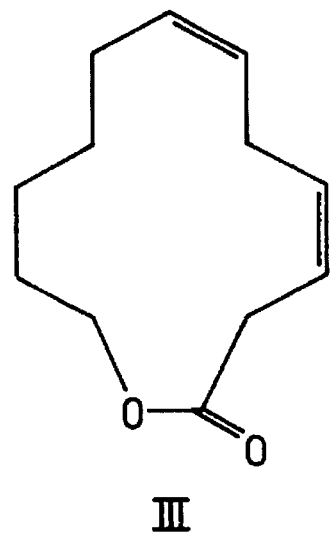
Figure 1:
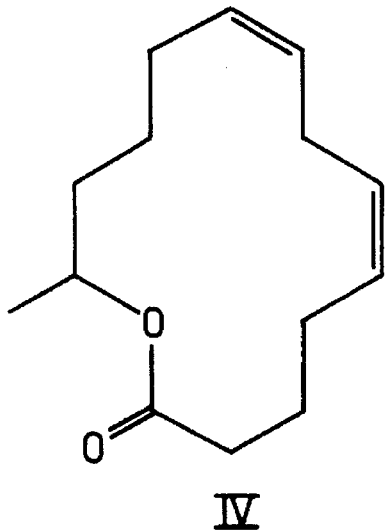

A novel preparation of II was undertaken including several novel steps, including the novel DEAD/PPh$_3$ cyclisation of hydroxy acid to provide the final product.

(a) 3-bromopropionaldehyde dimethyl acetal: acrolein (112 g, 2.00 mol) and dicinnamalacetone (100 mg) were dissolved in anhydrous dichloromethane (750 ml) and the solution cooled to 0° C.; anhydrous HBr (freshly generated and debrominated) was then bubbled through the solution until a persistent and uniform deep red colouration was observed (approx time 3 hours). Anhydrous methanol (102 ml, 2.5 mol), pTsOH (250 mg) and trimethyl orthoformate (270 ml, 2.5 mol) were added over 10 minutes at 0° C. whereupon considerable heat evolution was observed and an intense purple colour obtained. After stirring for 2 hours at 25° C. triethylamine was added (2 ml) and the resultant solution concentrated under 20–30 mm Hg vacuum <40° C. The residue was washed with water (50 ml), half saturated sodium bicarbonate solution (50 ml) and water (50 ml); the combined washings reextracted with pentane (100 ml) and the combined organics dried (MgSO$_4$) and concentrated as before. Distillation at reduced pressure through a 30 cm Vigreux column gave pure 3-bromopropionaldehyde dimethyl acetal as a colourless liquid (58° C.–60° C. at 14 mm Hg, 253.4 g, 1.385 mol, 69%).

(b) 5-hydroxyhexanal dimethyl acetal: magnesium turnings (7.3 g, 0.300 mol) were suspended in THF (350 ml) under nitrogen and 1,2-dibromoethane (2 ml) added; and after 5 minutes the suspension was cooled to 0° C. and the 3-bromopropionaldehyde acetal from (a) (45.88 g. 0.250 mol) was added at a rate sufficient to maintain the temperature in the range 5°–15° C. After a further 30 minutes at 10° C. the solution was added to a cooled (−30° C.) suspension of cuprous cyanide (2.24 g, 25.0 mmol, 10 mol %) in THF (100 ml) and propylene oxide (17.4 g, 0.300 mol) at such a rate as to maintain the temperature in the range −25° C. to −15° C. The resulting solution was allowed to warm to 25° C. and then quenched by the addition of half-saturated aqueous ammonium chloride solution (150 ml) and 33% aqueous ammonium hydroxide (15 ml). After stirring for 15 minutes the layers were separated and the aqueous one extracted with ether (2×150 ml) and the combined organics were washed with water (50 ml) and brine (100 ml), dried (MgSO$_4$) and concentrated. Purification by flash chromatography on silica gel (ether-light petroleum 1:1 eluant) gave 29.95 g, 184.6 mmol, 74% 5-hydroxyhexanal dimethyl acetal as a colourless oil. Attempts at distillation gave elimination of methanol so this product was used directly.

(c) 5-benzyloxyhexanal dimethyl acetal: a sodium hydride dispersion (7.2 g of 50% dispersion, 150 mmol, 1.2 equivalents) was washed with hexane (3×50 ml), suspended in DMF (250 ml) and cooled to 5° C. before adding the 5-hydroxyhexanal dimethyl acetal (20.28 g, 125.0 mmol) prepared in (b) in DMF solution (20 ml); the suspension being allowed to warm then up to 20° C. over 1 hour. After 30 minutes benzyl bromide (25.6 g, 150 mmol) was added at 5°–10° C. over 15 minutes and the resulting thick slurry quenched after 30 minutes by the careful addition of water (200 ml). Pentane (250 ml) was added and the layers separated, the aqueous phase was extracted with pentane (3×100 ml) and the combined pentane layers washed with water (2×100 ml) and brine (150 ml) dried (MgSO$_4$) and concentrated. Distillation gave pure 5-benzyloxyhexanal dimethyl acetal (101°–102° C. at 0.05 mm Hg, 122.4 mmol, 98%)

(d) 5-benzyloxyhexanal: the acetal from (c) (25.2 g, 100 mmol) was dissolved in THF (200 ml), propan-2-ol (20 ml) and water (100 ml) and pTsOH (500 mg) added. The resultant solution was refluxed for an hour and then diluted with pentane (2×100 ml) with the combined organics being washed with water (50 ml) and brine (100 ml), dried (MgSO$_4$) and concentrated to give the product (20.40 g, 99.0 mmol, 99% crude).

(e) 8-benzyloxy-(Z)-3-nonenal di-isopropyl acetal: 3,3-di-isopropoxypropyl triphenylphosphonium bromide (19.53 g, 37.7 mmol) (prepared from triphenylphosphine and acrolein using a modification of the procedure described by Santelli et al Synthesis, 395 (1988)) was suspended in THF (50 ml) and toluene (200 ml) under nitrogen, and sodium hexamethyldisilazide (17.18 ml of 1.92M solution in 1:4 THF-toluene, 33.0 mmol) added over 5 minutes at 0° C. Stirring at 25° C. for 2 hours was followed by cooling to −100° C. and addition of 5-benzyloxyhexanal (4.86 g, 23.56 mmol) from (d) in THF (20 ml) dropwise over 5 minutes. Stirring at −100° C. for 30 minutes and then warming to 25° C. over 3 hours, followed by quenching with half-saturated aqueous ammonium chloride solution (40 ml), extraction with ether (3×150 ml), washing of combined organics with water (2×50 ml) and brine (100 ml), drying (MgSO$_4$) and concentration gave a thick oil which was dissolved in dichloromethane (25 ml) and the solution poured into pentane (150 ml). Precipitated triphenylphosphine oxide was removed by filtration and reconcentration of the solution gave crude product that was purified by flash chromatography on silica gel (ether-light petroleum 1:9 eluant) (7.88 g, 22.62 mmol, 96%).

(f) 11-benzyloxy-dodeca-(3Z,6Z)-dienal di-isopropyl acetal: Product provided in (e) (4.182 g, 12.0 mmol) was dissolved in THF (120 ml) and warmed to reflux, pTsOH (6 ml of 0.1M aqueous solution) added and the resultant solution refluxed for 5 minutes before cooling to 0° C. Light petroleum (40 ml) was added followed by washing with water (2×20 ml) and brine (25 ml). The aqueous layers were reextracted with light-petroleum (30 ml) and the combined organics dried (MgSO$_4$) and concentrated. The resultant crude aldehyde was dissolved in THF (15 ml) and the solution added dropwise at −100° C. to a stirred solution of ylid obtained by stirring 3,3-di-isopropoxypropyl triphenylphosphonium bromide (10.02 g, 20.0 mmol, 1.66 equivalents) in THF (40 ml) and toluene (140 ml) with sodium hexamethyldisilazide (1.92M in THF-toluene 1:3, 9.25 ml, 17.8 mmol) at 20° C. for 1 hour. Warming to 0° C. over 4 hours was followed by quenching with half saturated aqueous ammonium chloride solution (25 ml) and the layers were then separated before extracting the aqueous layer with ether (2×30 ml). The combined organics were washed with water (10 ml) and brine (15 ml), dried (MgSO$_4$) and concentrated giving an oil which was then poured into pentane (100 ml). The precipitated triphenylphosphine oxide was removed by filtration and the filtrate concentrated to give crude 11-benzyloxy-dodeca-(3Z,6Z)-dienal di-isopropyl acetal which was purified by flash chromatography on silica gel (1:7 ether-light petroleum eluant) to give a colourless oil (4.04 g, 10.44 mmol, 87%).

(g) 11-hydroxy-dodeca-(3Z,6Z)-dienal di-isopropyl acetal: the benzyl ether from (f) (2.66 g, 6.84 mmol) was dissolved in THF (35 ml) and ammonia (30 ml) at −40° C. and t-butanol (5 ml) added. Lithium metal (300 mg, excess) was added to the resulting colourless solution until a persistent blue colour was obtained. Half saturated aqueous ammonium chloride solution (20ml) was slowly added followed by warming to 20° C. over 2 hours. Extraction with ether (3×40 ml) followed by washing the extracts with water (2×5 ml) and brine (20 ml), drying (MgSO$_4$) and concentration gave the crude alcohol. Purification by chromatography on silica gel (1:1 ether light petroleum eluant) gave the product acetal (1.91 g, 6.31 mmol, 93%)

(h) 11-hydroxy-dodeca-(3Z,6Z)-dienoic acid: the hydroxyacetal product from (g) was dissolved in THF (70 ml) and the solution warmed to reflux. pTsOH (1.75 ml of 0.1M aqueous solution) was added and after 10 minutes the solution was cooled to 0° C. and ether (50 ml) added. The layers were separated and the aqueous layer extracted with ether (3×40 ml). Combined ethereal layers were washed with water (15 ml) and brine (30 ml) and concentrated. The crude hydroxy aldehyde produced was dissolved in dichloromethane (40 ml) and 1-methylcyclohex-1-ene (2.50 g, 25.0 mmol) was added followed by water washing from the hydrolysis. The two phase mixture was cooled to 0° C. and sulphamic acid (5.0 ml of 1.0M aqueous solution) was added followed by sodium chlorite (15.3 ml of 1.0 ml aqueous solution) with rapid stirring. After 15 minutes the temperature was allowed to rise to 25° C. over 30 minutes; the layers were separated and the aqueous layer extracted with more dichloromethane (2×30 ml). The combined organic layers were concentrated and the residue redissolved in ether (30 ml). This solution was extracted with 0.5M sodium carbonate solution (3×25 ml) and the combined extracts washed with ether (20 ml), acidified to pH 1 with 2N HCl and then extracted with ether (3×30 ml). The combined ethereal extracts were washed with 2N HCl (10 ml), water (5 ml)and brine (20 ml), dried (MgSO$_4$) and concentrated to give the hydroxy acid product.

(i) 11-methyldodeca-(3Z,6Z)-dien-11-olide (Pheromone II): Triphenylphosphine (656 mg, 2.5 mmol) was dissolved in anhydrous deoxygenated toluene (200 ml) under nitrogen and DEAD (445 mg, 2.55 mmol) was added. After stirring for 5 minutes the hydroxy acid (h) (106 mg, 500 μmol) in toluene (30 ml) was added dropwise via a syringe drive over 9 hours with the addition of further triphenylphosphine (328 mg, 1.25 mmol) and DEAD (222 mg, 1.275 mmol) after 4 hours. On completion of addition the resulting mixture was stirred for a further hour and then concentrated. Purification by flash chromatography on silica gel (ether-light petroleum 1:39 eluant) gave II as a colourless oil (73 mg, 371 μmol, 74%).

EXAMPLE 2

Synthesis of (3Z,6Z)-tridecadien-13-olide (a) 6-hydroxyhexanal dimethyl acetal: 3-bromopropionaldehyde dimethylacetal (18.31 g, 100 mmol) was dissolved in THF(100 ml) and cuprous iodide (952 mg 50 mmol, 5 mol %) added; the suspension cooled to −15° C. and a warm (40° C.) 0.60M THF solution of 3-hydroxypropyl magnesium chloride chloromagnesium salt (166 ml, 100 mmol freshly prepared as described by Normant, Tetrahedron Lett, 3013 (1978) added over 15 min. After 30 minutes at −15° C. the suspension was warmed to 0° C. over 2 hours and saturated aqueous ammonium chloride solution (50 ml) and 33% aqueous ammonia (10 ml) added. After stirring for 15 minutes the layers were separated and the aqueous layers extracted with ether (2×100 ml): the combined organics were washed with water (30 ml) and brine (100 ml) dried (MgSO$_4$) and concentrated to give an oil. Purification by flash chromatography on silica gel (ether-lightpetroleum 1:1 eluant) gave the product as a colourless oil which eliminated methanol on attempted distillation (12.65 g 78.0 mmol, 78%);

(b) 6-benzyloxyhexanal dimethyl acetal: the hydroxyacetal from (a) (12.165 g, 75.0 mol) was benzylated using the same procedure as shown in Example 1(c) giving benzyloxy acetal as a colourless oil (102°–104° C. at 0.05 mm Hg 18.47 g, 73.2 mmol, 98%)

(c) 6-benzyloxyhexanal: Acetal product from (b) (14.01 g, 55.5 mmol) was hydrolysed by the same procedure as for 5-benzyloxyhexanal dimethyl acetal in Example 1, giving crude product as a colourless oil (10.98 g, 53.2 mmol, 98%)

(d) 9-benzyloxy-non-(3Z)-enal di-isopropyl acetal: Crude product from (c) (3.773 g, 18.29 mmol) was olefinated by the procedure described 5-benzyloxyhexanal in Example 1, giving a colourless oil (6.12 g, 17.56 mmol, 96%)

(e) 12-benzyloxy-dodeca-(3Z,6Z)-dienal isopropyl acetal: Benzyloxyacetal (5.14 g, 14.75 mmol) was homologated by the same method used for the conversion of 8-benzyloxy-(Z)-3-nonenal di-isopropyl acetal to the corresponding -(3Z,6Z)- compound described in Example 1 giving the product as a colourless oil (4.97 g, 12.80 mmol, 87%).

(f) 12-hydroxy-dodeca-(3Z,6Z)-dienal isopropyl acetal: The benzyl ether from (e) (3.15 g, 8.10 mmol) was reductively cleaved by the same procedure used for 11-benzyloxy-dodeca-(3Z,6Z)-dienal di-isopropyl acetal in Example 1 giving product as a colourless oil (2.17 g, 7.27 mmol, 90%).

(g) 12-hydroxy-dodeca-(3Z,6Z)-dienoic acid: The hydroxyacetal from (f) (2.417 g, 8.11 mmol) was hydrolysed and oxidised as described for the preparation of 11-hydroxy-dodeca-(3Z,6Z)-dienoic acid in Example 1, giving the acid product (1.412 g, 6.65 mmol, 82%) as a pale yellow oil.

(h) (3Z,6Z)-dodecadien-12-olide (III): Hydroxyacid from (g) (601 mg, 2.830 mmol) was dissolved in THF (20 ml) and half of the resulting solution was added dropwise over a period of 4 hours to a stirred solution of DEAD (2.531 g, 14.30 mmol) and triphenylphosphine (3.71 g, 14.10 mmol) in toluene (400 ml). Once addition had been completed further DEAD (1.263 g, 7.16 mmol) and triphenylphosphine (1.651 g, 7.04 mmol) were added, followed by addition of the remaining hydroxy acid solution over a further 4 hours. Workup was as for the lactonisation of II and gave crude III; purification by flash chromatogaphy on silica gel (ether-lightpetroleum 1:19 eluant) gave the pure lactone as a colourless oil (374 mg, 1.925 mmol, 68%).

EXAMPLE 3

Synthesis of 13-methyl-(5Z,8Z)-tetradecadien-13-olide (IV)

(a) 13-benzyloxy-tetradeca-(5Z,8Z)-dienoic acid:

8-benzyloxy-(Z)-3-nonenal di-isopropyl acetal (produced in Example 1) (3.485 g, 10 mmol) was hydrolysed using the general procedure given and the crude aldehyde dissolved in 10 ml of THF and added dropwise with precooling by contact with the flask walls at –100° C. to a solution of an ylid formed by stirring 4-carboxybutyl triphenylphosphonium bromide (8.86 g, 20 mmol) in THF (50 ml) and HMPA (8.5 ml) with a solution of NaHMDS in 1:3 THF-toluene (43.2 ml of 0.92M solution) at 25° C. for 2 hours. The resulting slurry was allowed to warm up for to 0° C. over 3–4 hours then quenched with saturated aqueous ammonium chloride solution (20 ml), acidified to phi with aqueous HCl and extracted with ether (3×50 ml). The combined extracts were washed with 2N HCl (10 ml) and brine (20 ml), dried ($Na_2SO_4$) and concentrated to give a thick oil. Purification by silica gel chromatography (ether-light petroleum-acetic acid 50:50:1 eluant) gave the acid product (1.94 g, 58.9 mmol, 59%).

(b) 13-hydroxy-tetradeca-(5Z,8Z)-dienoic acid: The benzyloxyacid from (a) (4.808 g, 14.55 mmol) was dissolved in 1:1 THF-ammonia (60 ml) at –40° C.:t-butanol (10 ml) was added followed by the piecewise addition of lithium metal (approx. 300 mg, excess) until a consistent dark blue colour was obtained. After 15 min the reaction was quenched by the addition of ammonium chloride (1 g); the resulting suspension was allowed to warm to 0° C. (with concomitant evaporation of ammonia) over 1 hour. Water (20 ml) was added followed by ether (30 ml): residual ammonium hydroxide was neutralised by addition of 2M HCl to pH1. The layers were separated and the aqueous layers extracted with ether (2×20 ml): the combined ethereal layers were washed with 2M HCl (10 ml) and brine (30 ml), dried ($MgSO_4$) and concentrated. Purification by flash chromatography on silica gel (ether-light-petroleum-aceticacid 50:50:1. eluant) gave the hydroxyacid product (3.158 g, 13.14 mmol, 90%) as a colourless oil.

(c) 13-methyl-(5Z,8Z)-tetradecadien-13-olide (IV): Triphenylphosphine (12.82 g, 48.9 mmol) was dissolved in toluene (950 ml) and DEAD (8.69 g, 49.9 mmol) added over 2 min. A solution of the hydroxyacid from (b) (2.350 g, 9.778 mmol) in toluene (50 ml) was added dropwise over 7 hours with the addition of more triphenylphosphine (6.41 g, 24.4 mmol) and DEAD (4.35 g, 25.0 mmol) after 4 hours. After stirring for a further 30 minutes the solvent was removed under reduced pressure and the residue dissolved in dichloromethane(30 ml): the resulting solution was poured into lightpetroleum (300 ml), resulting in the precipitation of an amorphous solid. The supernatant was filtered through a short column of silica gel, the precipitate redissolved in dichloromethane and the cycle repeated until no further product could be detected in the supernatant. The combined filtrates were concentrated and the residue purified by flash chromatography on silica gel (ether-lightpetroleum 1:24 eluant) to give IV as a colourless oil (1.543 g, 6.940 mmol, 70%).

EXAMPLE 4

Efficacy of Lure Compositions of the Invention

The bioassay used in this example was a simple single choice pitfall assay as used by Morgan and Healey ((1993) Proc. IOBC-WPRS). Beetles used were laboratory susceptible O. surinamensis strain all aged between 7–8 weeks when tested. The bioassay test was run for 1 hour in the dark with 10 or 15 replicates used for each treatment.

(a) Controls: Initial results showed that lactone III and racemates of lactone II and IV as prepared above provided 24%, 35% and capture at 1 µg, 2 µg and 2 µg per trap respectively (this taking into account any enantiomer specificity of II and IV). The R-enantiomer of II gave only 24% capture as opposed to an S- capture of 33%; the racemate giving a still higher value.

Aeration of the laboratory strain shows natural pheromone to comprise the pheromone lactones II, III and IV in 4:1:2 ratio, and the mixture 8:1:4 of synthetic pheromone (allowing for S/R dilution with racemates) proved to be attractive at 13–1300 ng (28–75% capture).

Although this demonstrates a good response the cost of production of such a lure is high; production costs of R,S-II being highest, decreasing for III and significantly less for R,S-IV; the natural ratio containing 57% II. R,S-IV on its own however is ineffective.

(b) Test of compositions of the invention:

| Test Number | Treatment II:III:IV | Weight (ng) | % Capture | Significance v control |
|---|---|---|---|---|
| 1 | CONTROL | — | 15 | |
| 2 | 8:1:4 | 130 | 68 | |
| 3 | R, S-II | 80 | 47 | p < 0.01 |
| 4 | 1:1:4 | 130 | 97 | p < 0.0001 |
| 5 | CONTROL | — | 12 | |
| 6 | 1:1:4 | 13 | 21 | p > 0.05 |
| 7 | *1:1:4 + 1-octen-3-ol | *13 | 68 | p < 0.0001 |
| 8 | 1:2:8 | 13 | 44 | p > 0.0001 |
| 9 | CONTROL | — | 10 | |
| 10 | 1:2:8 | 13 | 26 | p < 0.0001 |
| 11 | 1:2:8 + 1-octen-3-ol | *13 | 73 | p < 0.0001 |
| 12 | 1:2:8 + 1-octen-3-ol | *1.3 | 35 | p < 0.0001 |
| 13 | 1:2:8 + 1-octen-3-ol | *0.13 | 8 | p > 0.05 |
| 14 | CONTROL | — | 4 | |
| 15 | *1:2:8 + 1-octen-3-ol | *1.3 | 25 | p < 0.05 |
| 16 | *0:1:4 + 1-octen-3-ol | *1.3 | 39 | p < 0.0001 |
| 17 | *1:0:8 + 1-octen-3-ol | *1.3 | 21 | p < 0.01 |
| 18 | CONTROL | | 22 | |
| 19 | *0:0:1 + 1-octen-3-ol | *1.3 | 24 | p > 0.05 |
| 20 | *0:1:4 + 1-octen-3-ol | *1.3 | 51 | p < 0.0001 |
| 21 | *1:2:0 + 1-octen-3-ol | *1.3 | 37 | p < 0.05 |
| 22 | CONTROL | | 7 | |
| 23 | *0:1:4 + 1-octen-3-ol | *1.3 | 5 | p > 0.05 |
| 24 | *0:1:4 + 1-octen-3-ol | *130 | 73 | p < 0.0001 |
| 25 | *0:1:4 + 1-octen-3-ol | *1300 | 85 | p < 0.0001 |

*The weight columns above refer only to their content of pheromone lactones and not the 1-octen-3-ol which is present in ratio 1:4:28.8 as described as optimal in the description; eg. for test 23 7.5 ng fungal volatile is included; a ratio of 1:4:28.8 of III:IV:1-octen-3-ol.

Further tests were carried out using the preferred lure composition of the invention, ie. that containing III:IV and the 1-octen-3-ol only, in various amounts as applied to attractance of four strains.

Dosages of 0.013 ng to 130 ng per trap were assayed against attractancy for the laboratory susceptible strain, Faceby lodge strain, Burrington strain and St Mary's strain. The latter three strains were isolated as follows: Faceby Lodge was collected from a farm grain store and has been cultured since 1985; being resistant to chlorpyrifos-methyl, pirimphos methyl, fenitrothion, malathion, permethrin and etrimfos pesticides: Burrington was collected from a commercial grain store in 1988; being resistant to pirimiphos-methyl, chlorpyrifos-methyl and etrimfos: St Mary's was collected from a farm grain store and has been cultured since 1987; being resistant to chlorpyrifos-methyl, pirimiphos-methyl and etrimfos.

All strains were established using 200 unsexed adults resulting in a final average population density of 1500 insects per 50 grams of 5:5:1 by weight rolled oats, whole wheat flour, and brewers yeast. The insects were maintained in constant darkness at 25° C. Adults 4–5 weeks post eclosion and of mixed sex were removed and conditioned in darkness for 24 hours without food prior to testing and were held in a 75×25 mm glass tube with fluon around the inner top 25 mm to prevent the insects escaping. Five replicates of ten insects of each strain were used for each of five concentrations and the control.

Figure 2A:
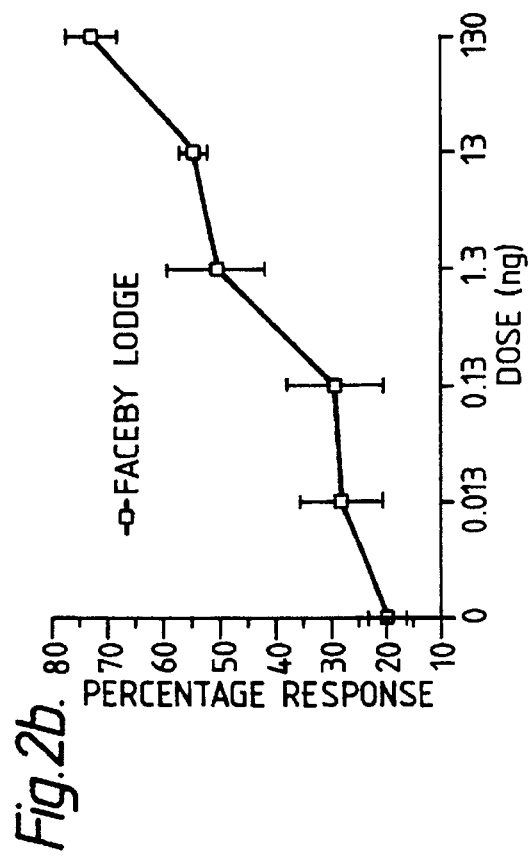
FIGS. 2a, 2b, 2c and 2d shows the results of capture experiments using a pit-fall olfactometer with lures of the composition of the invention employed against four strains of *O. surinamensis* with varying weight of lure.
Figure 2B:
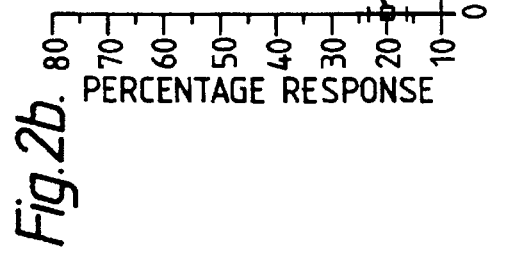
Figure 2C:
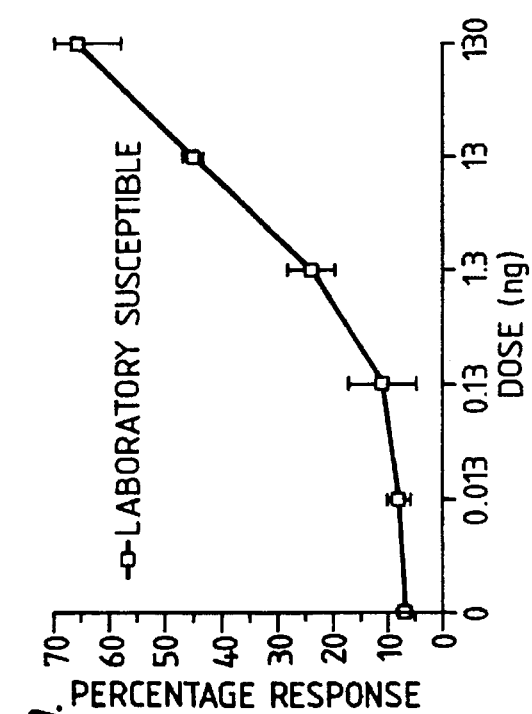
Figure 2D:
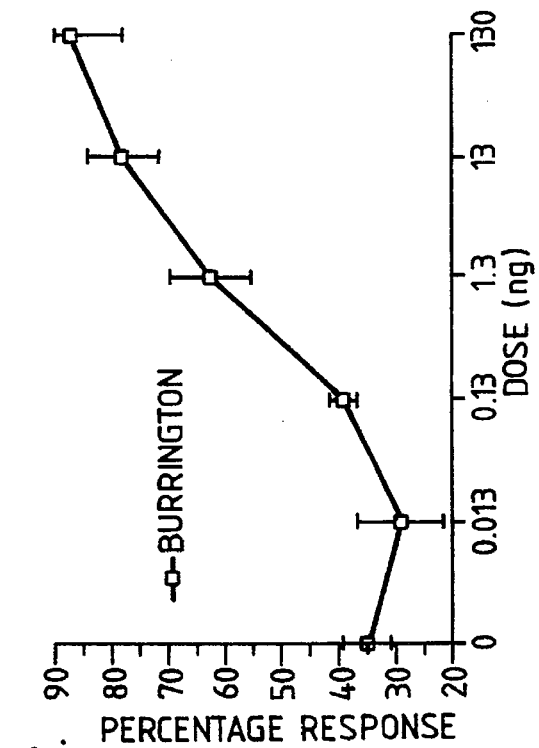
Figure 2D:
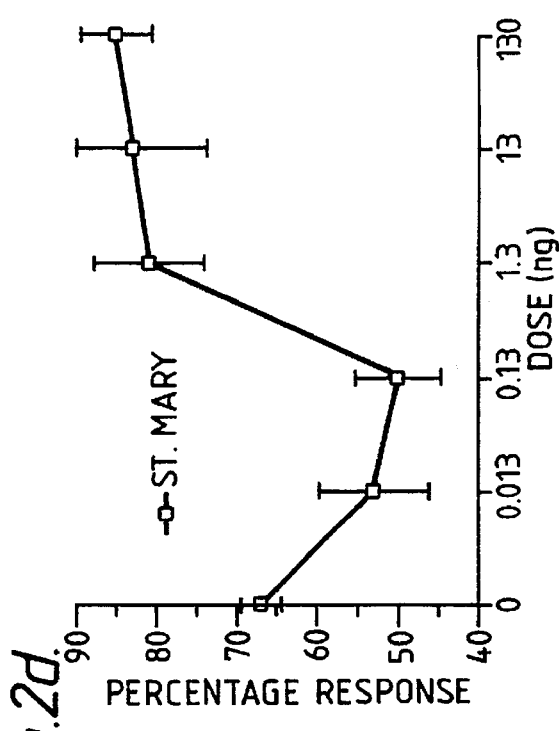

Bioassays were carried out using a single choice pitfall bioassay technique (Morgan and Healey, (1993) Proc. IOBC-WPRS) with a 3 hour assessment. All tests were conducted at the same time each day to minimise variability within days. The results were subjected to an arcsin transformation and analysed by t-test. Controls used hexane (HPLC grade) as the lures were employed as dissolved in 5 μl of hexane before airing for 1 minute to allow evaporation. Results of these tests are shown in FIG. 2.

We claim:

1. An *O. surinamensis* attractant composition consisting essentially of the pheromone lactone compounds (3Z,6Z)-dodecadien-12-olide and 13-methyl-(5Z,8Z)-tetradecadien-13-olide in a ratio by weight of about 1:4, and an attractant-enhancing amount of a fungal volatile selected from the group consisting of 1-octen-3-ol, 3-octanol and 3-methylbutanol.

2. An attractant composition for *O. surinamensis* consisting essentially of the pheromone lactone compounds (3Z,6Z)-dodecadien-12-olide and 13-methyl-(5Z,8Z)-tetradecadien-13-olide, together with the fungal volatile 1-octen-3-ol, wherein the ratio of (3Z,6Z)-dodecadien-12-olide to 13-methyl-(5Z,8Z)-tetradecadien-13-olide by weight is from 1:2 to 1:8 and the 1-octen-3-ol is present in the ratio of 5 to 10 parts by weight to 1.3 parts of the pheromone lactone compound.

3. A composition as claimed in claim 2 wherein the ratio of (3Z,6Z)-dodecadien-12-olide to 13-methyl-(5Z,8Z-tetradecadien-13-olide by weight is about 1:4.

4. A composition as claimed in claim 1 or claim 2 containing 1-octen-3-ol as fungal volatile, wherein the ratio of (3Z,6Z)-dodecadien-12-olide to 13-methyl-(5Z,8Z)-tetradecadien-13-olide to 1-octen-3-ol is about 1:4:20 to 1:4:40 by weight.

5. A composition as claimed in claim 4 wherein the ratio of (3Z,6Z)-dodecadien-12-olide to 13-methyl-(5Z,8Z)-tetradecadien-13-olide to 1-octen-3-ol is about 1:4:29 by weight.

6. An insect lure for attracting insects of species of *O. surinamensis*, consisting essentially of from 1.3 ng to 500 μg of a mixure of (3Z,6Z)-dodecadien-12-olide and 13-methyl-(5Z,8Z)-tetradecadien-13-olide in a 1:4 ratio by weight and from 7.5 ng to 3000 μg of 1-octen-3-ol.

7. An insect lure as claimed in claim 6 consisting essentially from 300 to 500 μg of a mixture of (3Z,6Z)-dodecadien-12-olide and 13-methyl-(5Z,8Z)-tetradecadien-13-olide, and from 1750 to 3000 μg of 1-octen-3-ol.

8. An insect lure for attracting insects of the species *O. surinamensis* consisting essentially of the pheromone lactone compounds (3Z,6Z)-dodecadien-12-olide and 13-methyl-(5Z,8Z)-tetradecadien-13-olide, together with the fungal volatile 1-octen-3-ol, wherein the ratio of (3Z, 6Z)-dodecadien-12-olide to 13-methyl-(5Z,8Z)-tetradecadien-13-olide by weight is from 1:2 to 1:8, the 1-octen-3-ol is present in the ratio of 5 to 10 parts by weight to 1.3 parts of the pheromone lactone compounds, and the composition is substantially completely devoid of 11-methyl-(3Z,6Z)-dodecadien-11-olide.

9. A composition as claimed in claim 8 wherein the ratio of (3Z,6Z)-dodecadien-12-olide to 13-methyl-(5Z,8Z)-tetradecadien-13-olide by weight is about 1:4.

10. The insect lure as claimed in claim 8 containing 1-octen-3-ol as fungal volatile, wherein the ratio of (3Z,6Z)-dodecadien-12-olide to 13-methyl-(5Z,8Z)-tetradecadien-13-olide to 1-octen-3-ol is about 1:4:20 to 1:4:40 by weight.

11. The insect lure as claimed in claim 10 wherein the ratio of (3Z,6Z)-dodecadien-12-olide to 13-methyl-(5Z,8Z)-tetradecadien-13-olide to 1-octen-3-ol is about 1:4:29 by weight.

12. A composition as claimed in claim 1 wherein the ratio of the pheromone lactones to the fungal volatiles is from 1:3.5 to 1:10.

13. A method of attracting *O. surinamensis* beetles comprising exposing to said beetles an attractant composition consisting essentially of the pheromone lactone compounds (3Z,6Z)-dodecadien-12-olide and 13-methyl-(5Z,8Z)-tetradecadien-13-olide in a ratio by weight of about 1:4, and an attractant-enhancing amount of a fungal volatile selected from the group consisting of 1-octen-3-ol, 3-octanol and 3-methylbutanol.

14. A method of attracting *O. surinamensis* beetles comprising exposing to said beetles an attractant composition consisting essentially of the pheromone lactone compounds (3Z,6Z)-dodecadien-12-olide and 13-methyl-(5Z,8Z)-tetradecadien-13-olide, together with the fungal volatile 1-octen-3-ol, wherein the ratio of (3Z,6Z)-dodecadien-12-olide to 13-methyl-(5Z,8Z)-tetradecadien-13-olide by weight is from 1:2 to 1:8, the 1-octen-3-ol is present in the ratio of 5 to 10 parts by weight to 1.3 parts of the pheromone lactone compounds.

15. A method as claimed in claim 14 wherein the ratio of (3Z,6Z)-dodecadien-12-olide to 13-methyl-(5Z,8Z)-tetradecadien-13-olide by weight is about 1:4.

16. A method as claimed in claim 13 or claim 14 containing 1-octen-3-ol as fungal volatile, wherein the ratio of (3Z,6Z)-dodecadien-12-olide to 13-methyl-(5Z,8Z)-tetradecadien-13-olide to 1-octen-3-ol is about 1:4:20 to 1:4:40 by weight.

17. A method as claimed in claim 16 wherein the ratio of (3Z,6Z)-dodecadien-12-olide to 13-methyl-(5Z,8Z)-tetradecadien-13-olide to 1-octen-3-ol is about 1:4:29 by weight.

18. A method for attracting insects of species of *O. surinamensis* comprising exposing said insects to a lure, consisting essentially of from 1.3 ng to 500 µg of a mixture of (3Z,6Z)-dodecadien-12-olide and 13-methyl-(5Z,8Z)-tetradecadien-13-olide in a 1:4 ratio by weight and from 7.5 ng to 3000 µg of 1-octen-3-ol.

19. The method as claimed in claim 18 consisting essentially from 300 to 500 µg of a mixture of (3Z,6Z)-dodecadien-12-olide and 13-methyl-(5Z,8Z)-tetradecadien-13-olide, and from 1750 to 3000 µg of 1-octen-3-ol.

20. A method for attracting insects of the species *O. surinamensis* comprising exposing said insects to a lure consisting essentially of the pheromone lactone compounds (3Z,6Z)-dodecadien-12-olide and 13-methyl-(5Z,8Z)-tetradecadien-13-olide, together with the fungal volatile 1-octen-3-ol, wherein the ratio of (3Z,6Z)-dodecadien-12-olide to 13-methyl-(5Z,8Z)-tetradecadien-13-olide by weight is from 1:2 to 1:8, the 1-octen-3-ol is present in the ratio of 5 to 10 parts by weight to 1.3 parts of the pheromone lactone compounds, and the composition is sibstantially completely devoid of 11-methyl-(3Z,6Z)-dodecadien-11-olide.

21. The method as claimed in claim 20 wherein the ratio of (3Z,6Z)-dodecadien-12-olide to 13-methyl-(5Z,8Z)-tetradecadien-13-olide by weight is about 1:4.

22. The method as claimed in claim 20 containing 1-octen-3-ol as fungal volatile, wherein the ratio of (3Z,6Z)-dodecadien-12-olide to 13-methyl-(5Z,8Z)-tetradecadien-13-olide to 1-octen-3-ol is about 1:4:20 to 1:4:40 by weight.

23. The method as claimed in claim 20 wherein the ratio of (3Z,6Z)-dodecadien-12-olide to 13-methyl-(5Z,8Z)-tetradecadien-13-olide to 1-octen-3-ol is about 1:4:29 by weight.

24. The method as claimed in claim 13 wherein the ratio of the pheromone lactones to the fungal volatiles is from 1:3.5 to 1:10.

* * * * *